United States Patent
Sakamoto et al.

(10) Patent No.: US 8,680,331 B2
(45) Date of Patent: Mar. 25, 2014

(54) PROCESS FOR PRODUCTION OF (METH)ACRYLIC ACID

(75) Inventors: Kazuhiko Sakamoto, Himeji (JP); Koji Ueno, Himeji (JP); Yoshitake Ishii, Himeji (JP); Satoshi Nakagawa, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 13/377,273

(22) PCT Filed: Jun. 24, 2010

(86) PCT No.: PCT/JP2010/060749
§ 371 (c)(1),
(2), (4) Date: Dec. 9, 2011

(87) PCT Pub. No.: WO2011/001891
PCT Pub. Date: Jan. 6, 2011

(65) Prior Publication Data
US 2012/0083624 A1    Apr. 5, 2012

(30) Foreign Application Priority Data
Jul. 1, 2009  (JP) .................. 2009-157060

(51) Int. Cl.
*C07C 51/42* (2006.01)
(52) U.S. Cl.
USPC ....................................... 562/600
(58) Field of Classification Search
CPC ..................................... C07C 51/43
See application file for complete search history.

(56) References Cited

U.S. PATENT DOCUMENTS

| 3,621,664 A | 11/1971 | Saxer |
| RE32,241 E | 9/1986 | Saxer |
| 5,504,247 A | 4/1996 | Saxer et al. |
| 5,546,763 A * | 8/1996 | Kikuchi et al. ............... 62/532 |
| 5,935,534 A | 8/1999 | Umino et al. |

FOREIGN PATENT DOCUMENTS

| JP | 53-41637 A | 4/1978 |
| JP | 53-41637 B | 11/1978 |
| JP | 7-48311 | 2/1995 |
| JP | 9-155101 | 6/1997 |

OTHER PUBLICATIONS

International Search Report issued Sep. 14, 2010 in International (PCT) Application No. PCT/JP2010/060749, of which the present application is the national stage.
Office Action dated Jul. 25, 2013 in corresponding Chinese Application No. 201080026408.6, with English translation thereof.

* cited by examiner

*Primary Examiner* — Paul A Zucker
(74) *Attorney, Agent, or Firm* — Wenderoth, Lind & Ponack, L.L.P.

(57) ABSTRACT

The objective of the present invention is to provide a process for production of (meth)acrylic acid with improved production efficiency by efficiently shifting from heating procedure to cooling procedure for a crystallizer. A process for production of (meth)acrylic acid according to the present invention is characterized in comprising the steps of crystallizing (meth)acrylic acid from a crude (meth)acrylic acid solution by using a batch type crystallizer, and melting the obtained (meth)acrylic acid crystal to obtain a (meth)acrylic acid melted liquid; wherein preliminary cooling of the crystallizer for the next crystallization step is started during transferring the (meth)acrylic acid melted liquid from the crystallizer.

4 Claims, 1 Drawing Sheet

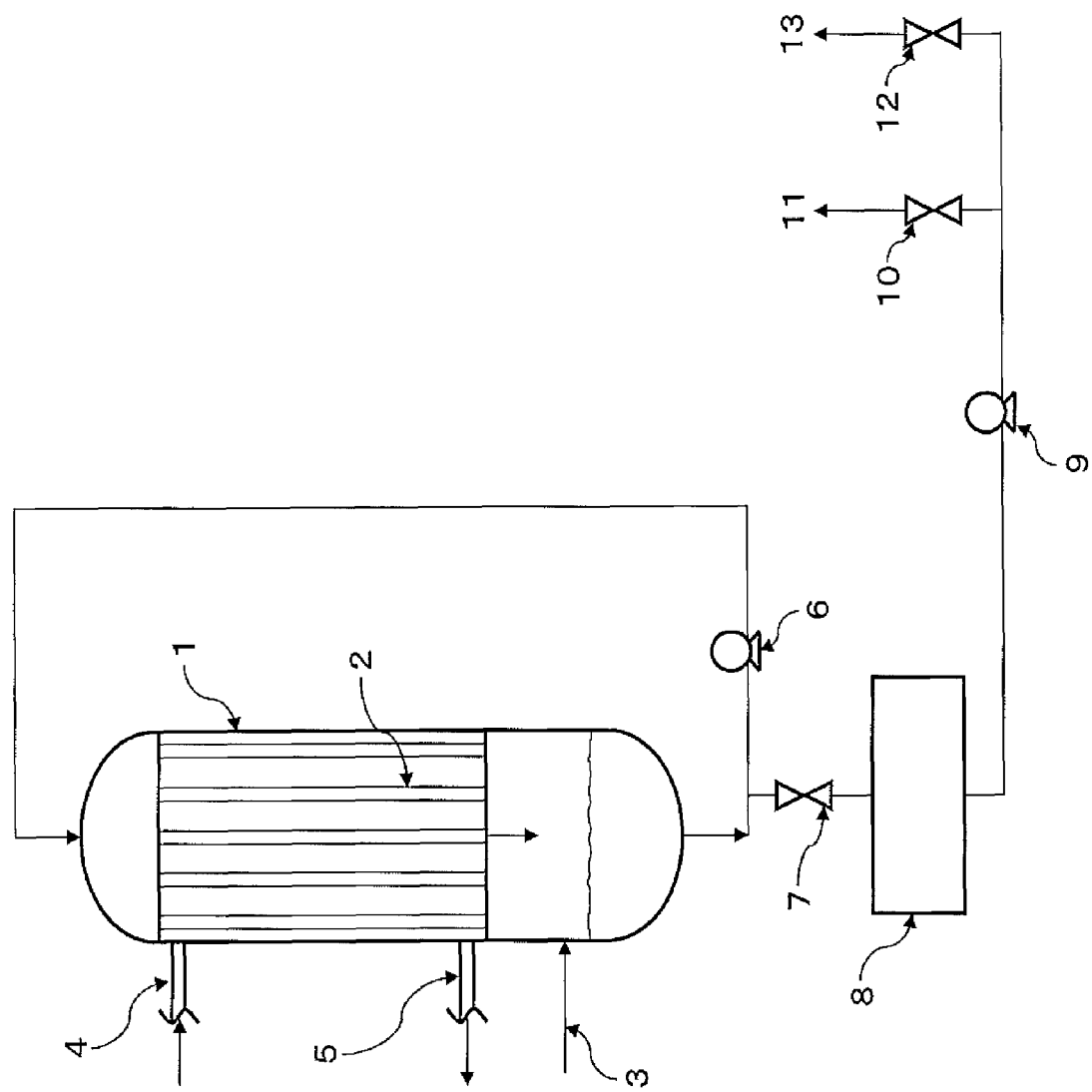

PROCESS FOR PRODUCTION OF (METH)ACRYLIC ACID

TECHNICAL FIELD

The present invention relates to a process for production of (meth)acrylic acid.

BACKGROUND ART

In general, (meth)acrylic acid is produced by the following steps:
- a gas containing (meth)acrylic acid is obtained by gas-phase oxidation reaction;
- the gas is supplied to a condensing tower or a collecting tower to obtain a crude (meth)acrylic acid solution;
- (meth)acrylic acid is purified from the crude solution.

As a purification method for (meth)acrylic acid, crystallization is used as well as distillation, diffusion, extraction and the like.

A gas containing (meth)acrylic acid obtained by gas-phase oxidation reaction contains by-products such as acetic acid and dimer as well as raw material compounds in addition to (meth)acrylic acid. Therefore, it is difficult to obtain (meth)acrylic acid having sufficiently high purity by only one time purification. In addition, it is necessary to combine various purification methods or repeat a purification method.

For example, acrylic acid or the like is crystallized a plurality of times to be purified in Patent Documents 1 and 2. In the processes described in the Patent Documents, tanks for respective crystallization stages are set up and the compounds stored in the respective tanks are used as raw materials for crystallization of the next stage. As the process, when purification by crystallization is repeated a plurality of times, a compound obtained in a stage is prevented from being mixed with a compound obtained in the previous stage since the compound obtained in the previous stage contains impurity in a larger amount. On the other hand, a crystallizer is more complicated in structure and more expensive than a tank; therefore, in general, a crystallizer is not necessarily set up for each crystallization stage although there may be some cases where the number of crystallizers is the same as the number of the repeating times of crystallization. For example, in the figures of Patent Documents 1 and 2, a plurality of tanks are described corresponding to the number of crystallization operations, but only one crystallizer is described.

Under the above-described circumstances, it is required to operate a crystallizer as efficiently as possible. However, there is no description about specific operation condition of a crystallizer for efficiently carrying out crystallization purification in Patent Documents 1 and 2.

In addition, it is general in crystallization purification to not only crystallize (meth)acrylic acid but also to melt the obtained crystal for transportation convenience. Therefore, in a crystallizer, both of a cooling energy for crystallizing (meth)acrylic acid from a crude (meth)acrylic acid solution and a heating energy for melting the (meth)acrylic acid crystal are needed.

PRIOR ART

Patent Document

Patent Document 1: JP-A-53-41637
Patent Document 2: JP-A-9-155101

DISCLOSURE OF THE INVENTION

Problems to be Solved by the Invention

As described above, it is required to repeat purification by crystallization and the like a plurality of times when (meth)acrylic acid is produced, since a lot of impurities are contained in a (meth)acrylic acid-containing gas obtained by gas-phase oxidation reaction. Nevertheless, it cannot be said that suitable conditions for efficiently carrying out heating and cooling in a crystallizer have been sufficiently studied so far.

On the other hand, a demand for (meth)acrylic acid has been growing more and more. The reason is thought to be aging of population in recent years, since (meth)acrylic acid is a raw material of a water-absorbing resin to be used for a diaper and the like. Consequently, a process for producing (meth)acrylic acid further efficiently is required.

Under the above-mentioned situation, the objective of the present invention is to provide a process for production of (meth)acrylic acid with improved production efficiency by effectively shifting from heating procedure to cooling procedure for a crystallizer.

Means for Solving the Problems

The inventors of the invention conducted various investigations to solve the above-mentioned problem. As a result, the inventors found that the smooth shift from a melting step to a crystallization step becomes possible by starting to change a heat medium from a heating medium needed for melting a (meth)acrylic acid crystal to a cooling medium needed for crystallizing (meth)acrylic acid in a crystallizer during the transfer of a melted liquid from the crystallizer, to complete the present invention.

The process for production of (meth)acrylic acid according to the present invention is characterized in comprising the steps of crystallizing (meth)acrylic acid from a crude (meth)acrylic acid solution by using a batch type crystallizer, and melting the obtained (meth)acrylic acid crystal to obtain a (meth)acrylic acid melted liquid;

wherein preliminary cooling of the crystallizer for the next crystallization step is started during transferring the (meth)acrylic acid melted liquid from the crystallizer.

BRIEF DESCRIPTION OF DRAWINGS

FIG. 1 is a drawing schematically showing a crystallizer for carrying out the production process of (meth)acrylic acid according to the present invention and peripheral facilities thereof. In the FIG. 1, "1" represents a crystallizer, "2" represents a crystallization tube, "3" represents a crude (meth)acrylic acid supply port, "4" represent a heat medium supply port, "5" represents a heat medium discharge port, "6" represents a circularly supplying pump, "7" represents a valve, "8" represents a middle storage tank, "9" represents a transfer pump, "10" represents a valve, "11" represents a line to a mother liquid tank for each crystallization purification stage, "12" represents a valve, and "13" represents a line to a (meth)acrylic acid tank for each crystallization purification stage.

MODE FOR CARRYING OUT THE INVENTION

Hereinafter, the process of the present invention is described in the order of operation.

The process of the present invention comprises the step of crystallizing (meth)acrylic acid from a crude (meth)acrylic acid solution by using a batch type crystallizer.

A crude (meth)acrylic acid solution is not particularly limited as long as it contains impurity in addition to (meth)acrylic acid as the objective compound. Such a crude solution is exemplified by a crude (meth)acrylic acid solution obtained by carrying out gas-phase oxidation reaction to obtain a (meth)acrylic acid-containing gas, and contacting the obtained gas with a collecting liquid or condensing the obtained gas. A crude (meth)acrylic acid solution obtained by contacting a (meth)acrylic acid-containing gas with a collecting liquid or condensing a (meth)acrylic acid-containing gas contains by-products such as water, acetic acid, propionic acid, maleic acid, acetone, acrolein, furfural, formaldehyde as well as (meth)acrylic acid and an unreacted raw material.

In order to obtain (meth)acrylic acid with higher purity, purification by crystallization may be repeated. Specifically, (meth)acrylic acid is crystallized to be purified, the purified (meth)acrylic acid is melted, and the obtained (meth)acrylic acid melted liquid is supplied to a crystallizer to repeat crystallization. In other words, crystallization purification may be repeated two or more times in the present invention. In the present invention, even purified (meth)acrylic acid obtained by carrying out crystallization one or more times is referred as crude (meth)acrylic acid for convenience when the (meth)acrylic acid is supplied to a crystallizer for crystallization to be further purified.

In the process of the present invention, (meth)acrylic acid is purified by crystallization using a crystallizer. The kind of a crystallizer is not particularly limited. However, since the objective of the invention is to efficiently carry out the shift from the melting step to the crystallization step in a single crystallizer, a crystallizer capable of carrying out both crystallization of (meth)acrylic acid and melting of the obtained crystal is used. For example, a crystallizer having a heat transfer face and capable of crystallizing and melting (meth)acrylic acid by heat exchange in the heat transfer face can be exemplified. In such a crystallizer, the inside thereof is preferably divided by a heat transfer face into a heat medium-existing part to which a cooling medium or a heating medium is supplied and a crystal-existing part where a crude (meth)acrylic acid solution and/or a (meth)acrylic acid crystal exists. In such a crystallizer, so-called dynamic crystallization can be carried out. In dynamic crystallization, a crude (meth)acrylic acid solution flows downward along a heat transfer face to be crystallized.

In the case that a crystallizer has a heat transfer face, (meth)acrylic acid is crystallized from a crude (meth)acrylic acid solution in the crystallization step and the crystallized (meth)acrylic acid is melted in the melting step by heat exchange on a heat transfer face. Specifically, in the crystallization step, a cooling medium is supplied to a crystallizer and at the same time, a (meth)acrylic acid solution is supplied to the crystallizer so that the crude (meth)acrylic acid solution is cooled by the cooling medium through a heat transfer face to crystallize (meth)acrylic acid. In the melting step, a heating medium is supplied to a crystallizer, and the crystallized (meth)acrylic acid is heated to be melted by the heating medium through a heat transfer face or by the heat of a circularly supplied (meth)acrylic acid melted liquid.

As a crystallizer having a heat transfer face, an apparatus commonly used as a heat exchanger may be employed. In particular, an apparatus to be used as a heat exchanger for carrying out heat exchange between liquids may be preferably used. Such a heat exchanger is exemplified by a plate-type heat exchanger, in which one plate or a plurality of plates at intervals are arranged so that a heat medium-existing part and a crystal-existing part are alternately formed through the plate(s); a multi-tubular type heat exchanger or a shell-and-tube type heat exchanger, in which a plurality of tubes are arranged for carrying out heat exchange between the outside and the inside of the tubes; and a double-tubular type heat exchanger, in which an inner tube is arranged in an outer tube so that heat exchange can be carried out between the inside and the outside of the inner tube. The cross-sectional shape of the tube to be used for a multi-tubular type heat exchanger and a double-tubular type heat exchanger is not particularly limited.

More specifically, for example, a static crystallizer manufactured by BEFSPROKEM (France) and a dynamic crystallizer manufactured by Sulzer Chemtech (Switzerland) can be employed. A dynamic crystallizer is preferably employed, since a crystal can be separated from a mother liquid more readily. The process of the present invention can be preferably applied for a Falling Film method. In a Falling Film method, crystallization is carried out by circularly supplying a crude (meth)acrylic acid solution to a crystallizer in batch manner and flowing the solution downward in a falling coating film-like state.

The melting point of acrylic acid is 13.5° C., and the melting point of methacrylic acid is 16° C. In the crystallization step, the freezing point of (meth)acrylic acid is lower than the melting points since a crude (meth)acrylic acid solution contains impurity; however, (meth)acrylic acid can be crystallized by sufficient cooling. A cooling procedure may be carried out step by step by the following reason. Specifically, it can be said that the purity of the objective compound crystal obtained at a relatively high temperature in a long time is higher than that of the compound crystal obtained at a relatively low temperature in a short time. In addition, it is known that when a crystal purity is heightened in an initial period of crystallization, the purity of the crystal grown thereafter can also be improved. Therefore, it is possible that the cooling temperature of a crude (meth)acrylic acid solution in an initial stage of crystallization is set to be relatively high to obtain a crystal having high purity and thereafter, the crystal is sufficiently grown by lowering the cooling temperature.

After the crystallization step, a (meth)acrylic acid crystal is separated from a solution, i.e. a mother liquid. In the case that a dynamic crystallizer is employed, dynamic crystallization is caused on a heat transfer face and the crystal is grown on the heat transfer face; on the other hand, the solution (the mother liquid) is discharged out from the heat transfer face.

The (meth)acrylic acid obtained in the crystallization step is subjected to the melting step. In the melting step, (meth)acrylic acid is liquefied for easy transfer. In addition, it also becomes easy to discharge the crystal out of a crystallizer. A sweating operation for increasing the purity may be arbitrarily carried out.

In the crystallization step, the amount of impurity existing in a solution is relatively increased as crystallization of (meth)acrylic acid progresses. As a result, the impurity is sometimes deposited on the surface of the (meth)acrylic acid crystal. Therefore, the purity of the crystal can be increased by partially melting the surface of the (meth)acrylic acid crystal and discharging the melted part. Such a partial melting treatment is called as sweating operation.

To carry out the sweating operation, a (meth)acrylic acid crystal may be partially melted by changing a heat medium to be introduced into a crystallizer from a cooling medium to a hating medium. For example, in the case an acrylic acid crystal is subjected to the sweating operation, the temperature of a heating medium may be set to be not less than the melting point of (meth)acrylic acid to melt not less than about 1% by mass and not more than 10% by mass of the crystal, and the melted liquid may be discharged. In the sweating operation, circulation of a mother liquid is stopped so as to avoid adhesion of impurity to a (meth)acrylic acid crystal. The melting degree of a crystal can be estimated based on, for example, an increase of a liquid in a storage part of a crystallizer.

The partially melted liquid obtained by the sweating operation may be combined with a mother liquid in the crystallization step, and the mixture may be further mixed with crude (meth)acrylic acid in order to be subjected to the crystallization step of "$n^{th}$" stage or "(less than n)$^{th}$" stage when the stage in which the partially melted liquid is obtained is defined as "$n^{th}$" stage. It is preferred that the partially melted liquid is mixed with crude (meth)acrylic acid and the mixture is subjected to the crystallization step of "$(n-1)^{th}$" stage.

With reference to FIG. 1, a mother liquid in the crystallization step is pooled in a storage part which corresponds to a lower part of the crystallizer 1. In the case that the sweating operation is carried out, a partially melted solution is also pooled in the storage part. The mixture of a mother liquid and a partially melted liquid can be transferred to the middle storage tank 8 by opening the valve 7. Further, the valve 10 is opened and the pump 9 is operated to transfer the mixture to mother liquid tanks for respective crystallization purification stages. Since the mixture contains (meth)acrylic acid, the mixture can be mixed with crude (meth)acrylic acid and subjected to crystallization purification to improve the yield.

After the crystallization step or the arbitrary sweating operation is carried out, a mother liquid and/or a partially melted liquid is completely discharged out of a crystallizer and then the temperature of a heating medium is increased to completely melt a (meth)acrylic acid crystal. Such a melting operation may be carried out by heating a (meth)acrylic acid crystal up to the melting point or higher. Similarly to the crystallization step, a plurality of heating media having different temperatures may be used for carrying out the melting step in a step-by-step manner. In the melting step, a melted liquid of (meth)acrylic acid may be circularly supplied. When a (meth)acrylic acid melted liquid is supplied to a crystallization tube, the melting operation can be facilitated by the heat of the melted liquid.

In FIG. 1, after completion of the melting step, the (meth)acrylic acid crystal existing in a crystallization tube 2 is completely melted and the melted liquid is pooled in the storage part which corresponds to a lower part of the crystallizer 1. The melted liquid is transferred to the middle storage tank 8 by opening the valve 7. Further, the valve 12 is opened and the pump 9 is operated so that the mixture is transferred to (meth)acrylic acid tanks for respective crystallization stages. If the purity of the obtained (meth)acrylic acid is not sufficient, the (meth)acrylic acid may be used as crude (meth)acrylic acid for the next crystallization purification stage. If the purity is sufficient, the (meth)acrylic acid may be regarded as a product.

The purification by crystallization described above may be repeated two or more times to obtain (meth)acrylic acid having further higher purity. The crystallization purification may be carried out preferably not less than 1 times and not more than 6 times, more preferably not less than 2 times and not more than 5 times, and even more preferably not less than 3 times and not more than 5 times.

In the case that the purification by crystallization is repeated twice or more, in general, tanks for storing (meth)acrylic acid purified in the respective crystallization stages are set up to store a (meth)acrylic acid until the amount becomes sufficient for use as a raw material for crystallization purification in the next stage.

When purification by crystallization is repeated a plurality of times, (meth)acrylic acid becomes easy to be polymerized, since the purity thereof is improved and also the concentration of a polymerization inhibitor added at the time of correcting or condensing a (meth)acrylic acid-containing gas to obtain a solution is lowered. In addition, heating procedure in the melting step increases the likelihood of polymerization. Therefore, it is preferable in the melting step to use a polymerization inhibitor.

A polymerization inhibitor is exemplified by a N-oxyl compound such as 2,2,6,6-tetramethylpiperidino-1-oxyl; a phenol compound such as p-methoxyphenol; a manganese salt compound such as manganese acetate; a dialkyldithiocarbamate salt compound such as copper dibutyldithiocarbamate; a nitroso compound; an amine compound; and a phenothiazine compound. In the case that one or more kinds of the polymerization inhibitors selected from the group consisting of the above-mentioned N-oxyl compound, phenol compound and manganese salt compound are used, it is made possible to obtain (meth)acrylic acid which has sufficiently high quality and is more excellent in color tone. Only one kind of a polymerization inhibitor may be singly used, or twice or more kinds of polymerization inhibitors may be used in combination.

A polymerization inhibitor may be directly added to a (meth)acrylic acid melted liquid or may be added in form of a solution. As a solvent for such a solution, a (meth)acrylic acid solution, water and acetic acid may be used. Among the examples, a (meth)acrylic acid solution is preferable.

Since a crystallizer to be used in the present invention is a batch type one, the (meth)acrylic acid purified in respective crystallization stages has to be transferred to a tank corresponding to the stage from a crystallizer before carrying out the next crystallization purification. However, it takes time for the transfer particularly in industrial mass production. Further, crystallization purification is repeatedly carried out in a crystallizer. Specifically, crystallization purification in the same stage may be repeated or crystallization purification in different stages may be carried out. In any cases, the crystallization step and the melting step are alternately carried out in one crystallizer. Therefore, it is required to alternately cool and heat a crystallizer. However, conventionally, the conditions for efficiently switching between such cooling procedure and heating procedure have not been studied.

In the present invention, during the melted liquid obtained by heating a (meth)acrylic acid crystal in the melting step is transferred from a crystallizer to a storage tank, preliminary cooling of the crystallizer is started for the next crystallization step. Specifically, even after melting of a (meth)acrylic acid crystal is completed, a heating medium for heating remains in a crystallizer immediately after the melting. Therefore, even when a cooling medium supply to the crystallizer is started for the next crystallization step by shifting a heat medium from a heating medium to a cooling medium, the crystallizer is not necessarily cooled immediately. More specifically, even if supply of a cooling medium to a crystallizer is started after melting of a crystal, the heat medium temperature at the heat medium supply port is significantly different from the heat medium temperature at the heat medium discharge port in the crystallizer due to a remaining heating medium and residual heat. The heat medium temperature at the heat medium discharge port is continuously decreased due to the supply of a cooling medium; however, it takes time until the temperature is stabilized. In the present invention, the time to simultaneously carry out transfer of a (meth)acrylic acid melted liquid from a crystallizer and cooling of a crystallizer is set so that the production efficiency can be improved.

In the present invention, the term "preliminary cooling" means that cooling of a crystallizer is started before crude (meth)acrylic acid is supplied into the crystallizer for the crystallization step to decrease the crystallizer temperature down to around the cooling medium temperature when the next crystallization is started. More specifically, the term means that after completion of the melting step, the heat medium to be supplied to a crystallizer for the next crystallization step is shifted from a heating medium to a cooling medium so that the temperature of a cooling medium introduced into the crystallizer is stabilized to be around the temperature of a cooling medium supplied for the crystallization step. The temperature of a cooling medium supplied to a crystallizer is preferably set to be a temperature in the range of ±5° C. of the temperature of a cooling medium supplied for the crystallization step. During the time from the melting step to the crystallization step, since no (meth)acrylic acid solution or crystal exists in a crystallization tube, the heat medium temperature at the heat medium supply port can be regarded as almost the same as the temperature of the crystallizer.

It is more preferred that the transfer of a (meth)acrylic acid melted liquid from a crystallizer is completed before the preliminary cooling is completed. Specifically, the preliminary cooling of a crystallizer for the next crystallization step is started during the transfer of the (meth)acrylic acid melted liquid from the crystallizer is completed, and before completion of the preliminary cooling, further the supply of crude (meth)acrylic acid as a raw material for the next crystallization step to a storage part of the crystallizer is started. As a result, by starting the circular supply of the crude (meth)acrylic acid in the storage part of the crystallizer immediately after completion of the preliminary cooling, the next crystallization step can be efficiently started. In the present invention, if a sufficient amount of a crude (meth)acrylic acid for circular supply exists in the storage part of a crystallizer, the circular supply, that is, the crystallization step, may be started even on the way that a prescribed amount of the crude (meth)acrylic acid is supplied into the storage part of the crystallizer.

It is preferred that at the moment when not less than 50% and not more than 90% of a (meth)acrylic acid melted liquid stored in the storage part of a crystallizer is transferred after the melting step, the preliminary cooling of the crystallizer is started. When the preliminary cooling is started when 90% or less of a (meth)acrylic acid melted liquid is transferred from a crystallizer, the shift from the melting step to the crystallization step can be carried out much efficiently. On the other hand, in the case that the preliminary cooling is started when less than 50% of a (meth)acrylic acid melted liquid is transferred from a crystallizer, it may be probably impossible that shift from the melting step to the crystallization step is efficiently carried out even if supply of a crude (meth) acrylic acid solution into a crystallizer is started immediately after completion of the transfer of a (meth) acrylic acid melted liquid from a crystallizer, since there is not the crude (meth) acrylic acid solution in an amount sufficient for circular supply in a storage part of the crystallizer at the time of completion of the preliminary cooling.

As described above, in the present invention process, a period to simultaneously carry out transfer of a melted liquid and the preliminary cooling of a crystallizer is provided so as to shorten the blank at the time of shift from the melting step to the crystallization step in the crystallizer as much as possible and accordingly, the production efficiency of (meth) acrylic acid can be improved.

EXAMPLES

Hereinafter, the present invention is described in detail with Examples. However, the present invention is not limited to the Examples in any way, and it is possible to carry out the present invention according to the Examples with an additional appropriate change within the range of the specification. Such a change is also included in the technical scope of the present invention.

Example 1

(1) Production of Crude Acrylic Acid Solution

Propylene was subjected to gas-phase oxidation reaction in a reactor. The obtained reaction gas was supplied into a collecting tower to be contacted with a collecting liquid to obtain a crude acrylic acid solution from the bottom of the collecting tower. The obtained crude acrylic acid solution was analyzed to find that the solution contained 90.0% by mass of acrylic acid, 3.2% by mass of water, 1.9% by mass of acetic acid, 0.6% by mass of maleic acid, 1.5% by mass of acrylic acid dimer, 0.07% by mass of furfural, 0.27% by mass of benzaldehyde, 0.06% by mass of formaldehyde, 0.1% by mass of hydroquinone, and 2.3% by mass of other impurities. The bottom temperature of the collecting tower at that time, which corresponds to the temperature of the crude acrylic acid solution immediately after taken out of the collecting tower, was 91° C.

After the temperature of the crude acrylic acid solution was adjusted to be about 25° C. by a heat exchanger, the solution was supplied to a storage part of the crystallizer 1 schematically shown in FIG. 1. More specifically, in the crystallizer 1, a crude acrylic acid solution could be circularly supplied to an upper part from a storage part by the circularly supplying pump 6. A tube for circular supply was a metal tube with a length of 6 m and an inner diameter of 70 mm. The crude acrylic acid solution supplied to the upper part dropped in a coating film-like state along the inner wall of the crystallization tube 2. The surface of the crystallization tube 2 was configured to have a double jacket structure, and a temperature was made controllable by a heat medium supplied from the heat medium supply port 4 and discharged through the heat medium discharge port 5. The crude acrylic acid which passed through the crystallization tube 2 was temporarily stored in the storage part and then, circularly supplied to the upper part in a continuous manner.

(2) First Crystallization Purification

A cooling medium was supplied to the above-mentioned crystallizer. When the temperature of the cooling medium near the heat medium supply port 4 of the crystallizer 1 became a temperature in the range of ±5° C. of the starting temperature of the crystallization step, circular supply of the crude acrylic acid solution from the storage part was started. The amount of the crystal crystallized on the inner wall of the crystallization tube 2 was estimated from the amount of the crude acrylic acid solution in the storage part, and the circulation was continued until about 60 to 90% by mass of the acrylic acid contained in the crude acrylic acid solution as the raw material was crystallized.

Next, the circularly supplying pump 6 was stopped, and a cooling medium was changed to a heating medium to sweat out about 2 to 5% by mass of the crystal. The sweating amount was estimated from the increase amount of the crude acrylic acid solution in the storage part. Thereafter, the valve 7 was opened and the sweat liquid in the storage part and the mother liquid at the time of crystallization were transferred to the middle storage tank 8. Further the valve 12 was opened to transfer the mixture to a first mother liquid tank.

Then, melting of the crystal on the inner wall surface of the crystallization tube 2 was started. From starting of the melting, the melted liquid was circularly supplied to the upper part of the crystallizer 1 using the pump 6 and flowed downward on the acrylic acid crystal in the crystallization tube to promote melting of the crystal. After the crystal was completely melted, the valve 7 was opened and the transfer of the melted liquid existing in the storage part to the middle storage tank 8 was started. At the time when about 70% of the entire melted liquid was transferred, the heating medium supplied to the crystallizer 1 was changed to a cooling medium, and thus the transfer of the melted liquid and the cooling of the crystallization tube 2 were simultaneously carried out. Before the temperature of the cooling medium near the heat medium supply port 4 of the crystallizer 1 was stabilized in the range of ±5° C. of the starting temperature of the crystallization step, the transfer of the entire amount of the melted liquid was completed. Thereafter, the valve 10 was opened and the melted liquid was transferred to a first acrylic acid tank.

(3) Second Crystallization Purification

Immediately after completion of the transfer of the entire amount of the melted liquid from the crystallizer 1, the whole amount of acrylic acid in the first acrylic acid tank was supplied to the crystallizer 1 and subjected to purification by crystallization similarly to the above-described first crystallization purification. Then, the acrylic acid was transferred to a second acrylic acid tank. At the time when the temperature of the cooling medium near the heat medium supply port 4 was stabilized in the range of ±5° C. of the starting temperature of the crystallization step, a sufficient amount of crude acrylic acid was stored in the storage part of the crystallizer 1. As a result, circular supply of the crude acrylic acid could be quickly started and thus, it was possible to efficiently shift to the second crystallization purification.

(4) Third Crystallization Purification

Immediately after completion of the transfer of the entire amount of the melted liquid from the crystallizer 1, the whole amount of acrylic acid in the second acrylic acid tank was supplied to the crystallizer 1 and subjected to purification by crystallization similarly to the above-described first crystallization purification. However, in the melting step, an acrylic acid solution containing 5% by mass of p-methoxyphenol as a polymerization inhibitor was fed to the storage part of the crystallizer 1, and then the mixture was flowed downward on the acrylic acid crystal in the crystallization tube. The obtained acrylic acid was transferred to a third acrylic acid tank.

(5) Fourth Crystallization Purification

Immediately after completion of the transfer of the entire amount of the melted liquid from the crystallizer 1, the whole amount of acrylic acid in the third acrylic acid tank was supplied to the crystallizer 1 and subjected to purification by crystallization under a condition similar to the third crystallization purification. Then, the obtained acrylic acid was transferred to a fourth acrylic acid tank.

The obtained purified acrylic acid was analyzed; as a result, it was found that the acrylic acid had a purity of 99.94% by mass, and additionally contained 94 ppm by mass of water, 440 ppm by mass of acetic acid, 2 ppm by mass of maleic acid, 47 ppm by mass of acrylic acid dimer, 0.2 ppm by mass of furfural, and 0.1 ppm by mass of benzaldehyde, and no formaldehyde was detected. The production efficiency from the first crystallization purification to the fourth crystallization purification was 3.68 kg/h.

Comparative Example 1

Acrylic acid was purified by the same manner as Example 1, except that after the first crystallization purification was completed and then the whole amount of the acrylic acid in the crystallizer 1 was transferred to the middle storage tank 8, the cooling of the crystallization tube 2 was started by changing the heat medium which was supplied into the crystallizer 1 from a heating medium to a cooling medium.

The purified acrylic acid to be obtained was analyzed; as a result, it was found that the acrylic acid had a purity of 99.94% by mass, and additionally contained 92 ppm by mass of water, 460 ppm by mass of acetic acid, 2 ppm by mass of maleic acid, 51 ppm by mass of acrylic acid dimer, 0.3 ppm by mass of furfural, and 0.2 ppm by mass of benzaldehyde, and no formaldehyde was detected. The production efficiency from the first crystallization purification to the fourth crystallization purification was 3.32 kg/h.

As described above, in the case that the preparation for the crystallization step, that is, cooling of a crystallizer, was started after the whole amount of acrylic acid melted in the melting step was transferred from the crystallizer, the production efficiency was low. On the other hand, when the cooling of a crystallizer was started during the transfer of an acrylic acid melted liquid from the crystallizer, the production efficiency was obviously improved though the purity of the purified acrylic acid was approximately the same.

Consequently, according to the present invention process, (meth)acrylic acid can be produced much efficiently.

INDUSTRIAL APPLICABILITY

According to the present invention process, when (meth)acrylic acid is purified by crystallization, it is made possible to smoothly carry out the shift from the melting step to the crystallization step. In addition, there is no need to add any particular facility when the present invention process is carried out. Therefore, the process of the present invention is industrially remarkably advantageous for improving the production efficiency of (meth)acrylic acid.

The invention claimed is:

1. A process for production of (meth)acrylic acid, comprising the steps of crystallizing (meth)acrylic acid from a crude (meth)acrylic acid solution with a batch type crystallizer to obtain a (meth)acrylic acid crystal, and melting the obtained (meth)acrylic acid crystal to obtain a (meth)acrylic acid melted liquid;
wherein the (meth)acrylic acid melted liquid is pooled in a storage part of the crystallizer, and preliminary cooling of the crystallizer for a next crystallization step is started during transferring of the pooled (meth)acrylic acid melted liquid from the crystallizer.

2. The production process according to claim 1, wherein the transfer of the pooled (meth)acrylic acid melted liquid from the crystallizer is completed before completion of the preliminary cooling.

3. The production process according to claim 1, wherein the preliminary cooling of the crystallizer is started when not less than 50% and not more than 90% of the pooled (meth)acrylic acid melted liquid is transferred from the crystallizer.

4. The production process according to claim 2, wherein the preliminary cooling of the crystallizer is started when not less than 50% and not more than 90% of the pooled (meth)acrylic acid melted liquid is transferred from the crystallizer.

* * * * *